United States Patent
Fischer et al.

(10) Patent No.: US 8,216,153 B2
(45) Date of Patent: Jul. 10, 2012

(54) CRYOBIOPSY PROBE

(75) Inventors: Klaus Fischer, Nagold (DE); Mara Szyrach, Tübingen (DE); Daniel Schäller, Tübingen (DE); Matthias Voigtländer, Gomaringen (DE); Irina Sigle, Mössingen (DE)

(73) Assignee: ERBE Elektromedizin GmbH, Tübingen (DE)

( * ) Notice: Subject to any disclaimer, the term of this patent is extended or adjusted under 35 U.S.C. 154(b) by 198 days.

(21) Appl. No.: 12/666,147

(22) PCT Filed: Jun. 20, 2008

(86) PCT No.: PCT/EP2008/005010
§ 371 (c)(1),
(2), (4) Date: Feb. 24, 2010

(87) PCT Pub. No.: WO2009/000477
PCT Pub. Date: Dec. 31, 2008

(65) Prior Publication Data
US 2010/0198202 A1   Aug. 5, 2010

(30) Foreign Application Priority Data

Jun. 26, 2007 (DE) .......................... 10 2007 029 387
Jun. 4, 2008 (DE) .......................... 10 2008 026 635

(51) Int. Cl.
*A61B 10/00* (2006.01)
*A61B 18/18* (2006.01)
*A61F 7/00* (2006.01)
*A61F 7/12* (2006.01)

(52) U.S. Cl. ............ 600/562; 600/568; 606/20; 606/21; 606/22; 606/23; 607/96; 607/113

(58) Field of Classification Search .................. 600/562, 600/568; 606/20–23; 607/96, 113
See application file for complete search history.

(56) References Cited

U.S. PATENT DOCUMENTS

| 3,439,680 | A | * | 4/1969 | Thomas, Jr. .................... 606/24 |
| 5,133,360 | A | * | 7/1992 | Spears ........................... 600/567 |
| 5,353,804 | A | * | 10/1994 | Kornberg et al. ............. 600/567 |
| 5,928,164 | A | * | 7/1999 | Burbank et al. .............. 600/567 |
| 6,032,675 | A | * | 3/2000 | Rubinsky ...................... 128/898 |
| 6,193,644 | B1 | * | 2/2001 | Dobak et al. ................... 600/23 |
| 6,238,355 | B1 | * | 5/2001 | Daum ........................... 600/567 |
| 6,379,348 | B1 |   | 4/2002 | Onik |
| 6,488,673 | B1 | * | 12/2002 | Laufer et al. .................. 604/516 |

(Continued)

FOREIGN PATENT DOCUMENTS

EP        0 119 176 A2        9/1984

(Continued)

*Primary Examiner* — Sean Dougherty
(74) *Attorney, Agent, or Firm* — Dickstein Shapiro LLP

(57) ABSTRACT

A cryosurgical instrument for separating a tissue sample from a biological tissue to be treated, for purposes of biopsy. The cryosurgical instrument includes a probe for bringing a probe head up to the biological tissue and a gas line for supplying cooling gas from a gas source of a cryosurgical apparatus to the probe head. The probe head cools a limited tissue region, by means of the supplied gas, for obtaining a tissue sample. The tissue sample can be separated from the surrounding tissue when frozen onto the probe head. The instrument has a support tube in which the probe is guided and which can be moved relative to the probe in such a way that the surrounding tissue can be supported by means of the support tube during the separating of the tissue sample. The instrument also includes an accelerating device that provides a predefined force for the separating process.

14 Claims, 3 Drawing Sheets

U.S. PATENT DOCUMENTS

| | | | |
|---|---|---|---|
| 6,527,765 B2 * | 3/2003 | Kelman et al. | 606/22 |
| 6,540,694 B1 * | 4/2003 | Van Bladel et al. | 600/564 |
| 6,551,255 B2 * | 4/2003 | Van Bladel et al. | 600/584 |
| 6,772,766 B2 * | 8/2004 | Gallo et al. | 128/898 |
| 7,556,624 B2 * | 7/2009 | Laufer et al. | 604/514 |
| 2003/0125722 A1 * | 7/2003 | Gallo et al. | 606/21 |
| 2003/0181896 A1 * | 9/2003 | Zvuloni et al. | 606/20 |
| 2003/0195436 A1 | 10/2003 | Van Bladel et al. | |
| 2006/0009712 A1 * | 1/2006 | Van Bladel et al. | 600/566 |
| 2007/0083129 A1 | 4/2007 | Mark | |
| 2007/0287933 A1 * | 12/2007 | Phan et al. | 600/566 |
| 2008/0103411 A1 * | 5/2008 | Van Bladel et al. | 600/564 |
| 2010/0041949 A1 * | 2/2010 | Tolkowsky | 600/109 |
| 2010/0152722 A1 * | 6/2010 | Kleinberger | 606/21 |
| 2011/0071427 A1 * | 3/2011 | Fischer et al. | 600/565 |

FOREIGN PATENT DOCUMENTS

| | | |
|---|---|---|
| WO | WO 2007/025106 A2 | 3/2007 |
| WO | WO 2008/074422 A1 | 6/2008 |
| WO | WO 2010049056 A1 * | 5/2010 |

* cited by examiner

CRYOBIOPSY PROBE

FIELD OF THE DISCLOSED EMBODIMENTS

The disclosed embodiments relate to a cryosurgical instrument for obtaining a tissue sample, and in particular to a cryobiopsy probe.

BACKGROUND

Cryobiopsy is a special method in the field of endoscopy for withdrawing tissue samples from a patient's body and thus not only for facilitating, but also for improving, the diagnosis regarding any symptoms.

The withdrawing process in a cryobiopsy procedure proceeds as follows. A cryoprobe is placed with slight pressure onto the tissue to be examined. The tissue is frozen onto the probe at this point by intensive cooling of the probe head. After a given time, the frozen-on tissue is extracted from the probe by way of a mechanical pull.

The rapid and intensive cooling of the probe head (approx. −50° C.) is achieved by way of the Joule-Thomson effect. This effect draws on the fact that gas cools intensively when it can expand under high pressure through a small nozzle into a large space. This expansion takes place in the probe head. The expansion of the gas produces energy in the form of cold.

Different apparatuses are known for carrying out a cryobiopsy. One such cryosurgical apparatus is described in United States Patent Application Publication No. 2003/0195436 A1. This instrument is particularly suitable for the inspecting and "coring" of tumors. The instrument includes a handle which is connected to a probe. The probe has a probe head having a lance-shaped configuration at its distal end. The probe head may, as described, be intensively cooled. Furthermore, the instrument has a withdrawal cannula. For the purposes of withdrawal, the tissue is speared using the lance or the probe head and frozen solid thereon. A part of the frozen-solid tissue is cut out of the tumour by advancing the withdrawal cannula. The cut-out tissue sample can be withdrawn by detaching the instrument. In order to facilitate the cutting-out process, the device described in US 2003/0195436 A1 includes an accelerating device which is driven by a spring and drives the cannula into the tissue at a predetermined force.

This cryosurgical instrument is not suitable for withdrawing tissue samples at tissue surfaces. Furthermore, it may be used to withdraw only relatively large amounts of tissue. The corresponding method thus causes serious damage to the tissue to be treated.

SUMMARY

Starting from this prior art, the object of the disclosed embodiments is to provide an improved cryosurgical instrument. The instrument is in particular to be suitable for withdrawing tissue samples from tissue walls, and in particular from mucous membranes. This should lead to as little damage as possible to the surrounding tissue and the sample should be preserved per se in as good condition as possible. The withdrawing process should be simple and efficient. The instrument of the disclosed embodiments thus allows a tissue sample to be withdrawn in a reliable manner that is gentle on the tissue and provides a high degree of safety to the patient.

Disclosed embodiments include a cryosurgical instrument for obtaining a tissue sample, the instrument including a probe with a probe head which can be cooled by a cooling means for fixing a portion of a tissue wall; a support tube with a distal end, the probe being mounted in the support tube so as to be movable relative thereto; and an accelerating device for accelerating the support tube at a predetermined acceleration force relative to the probe, the acceleration force being directed such that the probe is retracted into the interior of the support tube from an extended position in which the probe head protrudes beyond the distal end of the support tube, wherein the distal end of the support tube is configured such that it induces, in the event of contacting of the tissue wall, a tear-off force such that the probe tears off a portion of the tissue wall.

In the disclosed embodiments, the tissue sample or the biopsate is not cut out of the tissue wall, but is torn out by a clearly defined force. For this purpose, according to the disclosed embodiments, the probe head is frozen onto the tissue wall and then retracted into the support tube with a tear-off force. In order to be able to carry out the tearing-off process successfully, it is necessary to exert a suitable pulse on the frozen-on tissue. For the doctor carrying out the treatment, it is problematic to exert the suitable pulse by means of the probe head. The disclosed embodiments provide the accelerating device for this purpose. The accelerating device accelerates the support tube relative to the probe. The striking of the accelerated support tube on the tissue wall releases a tear-off force, by means of which the probe head tears out a region of the tissue wall. The tear-off force acts substantially in the opposite direction to the acceleration force which is exerted on the support tube. The tearing-out provides advantageous separating of the tissue that takes natural cell boundaries into account.

The probe head may include a planar portion for contacting with the tissue. This portion extends substantially perpendicularly to the longitudinal axis of the probe and is configured to allow as extensive contacting as possible with the tissue wall. The planar portion may either be flat or have any other suitable surface structure. For example, the probe head could be slightly rounded-off. It is crucial that an extensive contact area, which is frozen solid on the planar portion by way of the cooling using the cooling means, be produced when the probe head is pressed onto the tissue. The tear-off force may thus easily be transmitted to the tissue.

The accelerating device may include a pneumatic and/or an electromagnetic and/or a mechanical and/or a pyrotechnical accelerating device. A predefined acceleration force may thus be provided. The defined tear-off force leads to advantageous results during the triggering of biopsate. The doctor does not have to set the suitable pulse by hand. The same amount of force is applied during each biopsy.

The accelerating device may also include a spring. The spring may be tensioned prior to engagement and stores a defined amount of potential energy.

The accelerating device may also include a connecting piece which is operatively connected to the support tube and is coupled indirectly or directly to the probe. The connecting piece includes a tensioning element which stores a predetermined amount of potential energy. Preferably, the above-described spring is mounted inside the connecting piece.

The accelerating device may also include a triggering device which releases the potential energy. The withdrawing process may thus be carried out by pressing a button.

The cryosurgical instrument may include a gripping piece, wherein the probe and/or the support tube is detachably coupled to the gripping piece. It is thus possible to configure the support tube and/or probe as single-use apparatuses, while the gripping piece is reusable.

The cryosurgical instrument may be configured such that the overhang of the probe head is at least 5 mm, and in particular is 15 mm, in the extended position. This distance ensures that the tip of the probe is clearly visible. During the freezing process, the doctor has a good view of the probe head and the position thereof. The distance from the probe head to the closing plane of the distal end of the support tube is designated as the overhang.

The support tube may be made of plastics material. The use of plastics material allows sufficient buckling strength of the support tube to be obtained, so that the support tube does not collapse during the tearing-off process. Furthermore, plastics material has the advantage of being a heat insulator. This prevents the distal end of the protective tube from freezing onto the tissue during cooling of the probe head.

The probe head may be made of a metallic material.

BRIEF DESCRIPTION OF THE DRAWINGS

The disclosed embodiments will be described hereinafter based on example embodiments which will be illustrated in greater detail with reference to the enclosed drawings.

DETAILED DESCRIPTION

Figure 1:
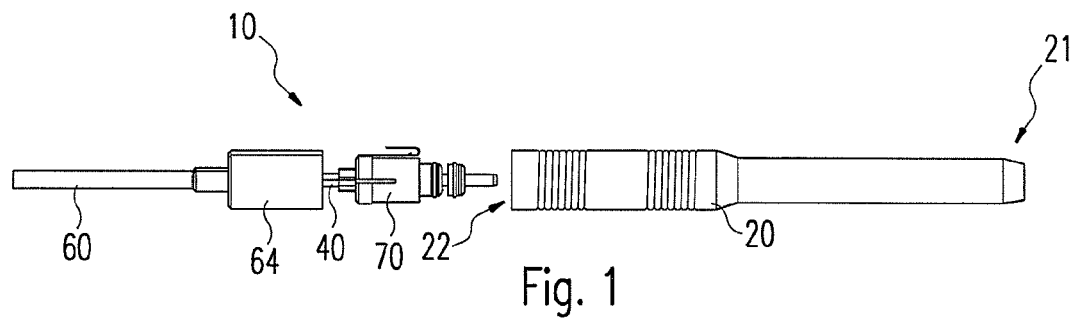
FIG. 1 illustrates a cryosurgical instrument according to a disclosed embodiment.

The same reference numerals will be used in the following description for identical and equivalent parts.

The cryosurgical instrument according to disclosed embodiments consists of three basic assemblies, as shown in FIG. 1. These three assemblies are the support tube 60 with the connecting piece 64, the coupling unit 70 with the probe 40, and gripping means 20. The support tube 60 with the connecting piece 64 serves as a protector and for releasing the biopsate. The protective tube 60 is movably fixed to the coupling unit 70 by means of the connecting piece 64. The coupling unit 70, which includes a leaf spring 112, forms a part of the accelerating device 110 (FIG. 8-12). The gripping means 20 is for holding the electrosurgical instrument 10.

Couplings between the individual assemblies allow the individual parts of the cryosurgical instrument 10 to be detached and to be exchanged or cleaned as required. Thus, the system is flexible and more attractive for handling than completely closed systems. The gripping means 20 has a proximal end 21 and a distal end 22. The coupling unit 60 is connected to the gripping means 20 at the distal end 22.

Figure 2:
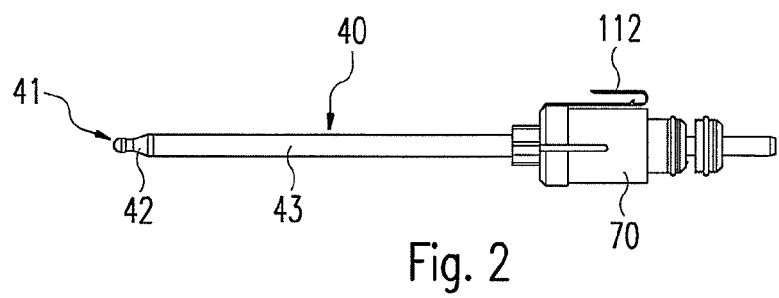
FIG. 2 illustrates a cryoprobe according to a disclosed embodiment.

FIG. 2 shows the probe 40 in detail. The probe is composed of a probe head 42, a probe body 43 and the coupling unit 70. The distal end 41 of the probe 40 is therefore formed by the probe head 42 which is adhesively bonded to the probe body 43. This probe body 43 is connected at the proximal end of the probe 40 to the coupling unit 70 which includes a leaf spring 112 for triggering the accelerating device 110 (FIG. 8-12).

Figure 3:
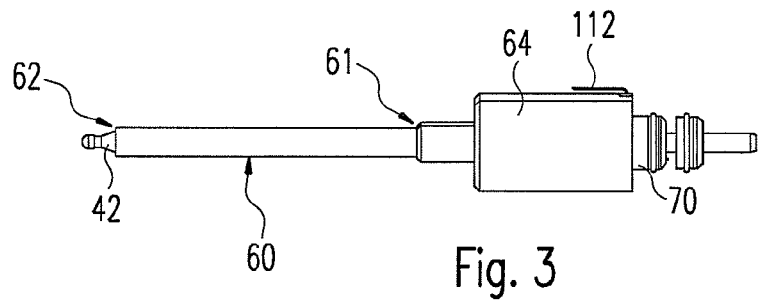
FIG. 3 illustrates the cryoprobe of FIG. 2 with a protective tube.

FIG. 3 shows the probe 40 from FIG. 2 with the support tube 60. The support tube is, as previously described, connected at its proximal end 61 to a connecting piece 64. The connecting piece 64 has a cylindrical shape and may be slid partially over the coupling unit 70. During sliding-over, a portion of the leaf spring 112 engages with a corresponding opening of the connecting piece 64. A cavity 66 (cf. FIG. 4), in which a spiral spring 114 (cf. FIG. 8) is arranged, is located inside the connecting piece 64. This spiral spring 114 is tensioned by pulling over the connecting piece 64. On actuation of the leaf spring 112, the leaf spring 112 becomes detached from the opening on the connecting piece 64 and releases the potential energy stored in the tensioned spiral spring 114. The connecting piece 64 with the support tube 60 is, as a result, accelerated relative to the coupling unit 70 with the probe 40 in the distal direction. As shown in FIG. 3, the probe head 42 protrudes, in the engaged state, several millimeters beyond the distal end 62 of the protective tube 60. On triggering of the pre-tensioned spring 114, the support tube 60 is slid over the probe head 42.

Figure 4:
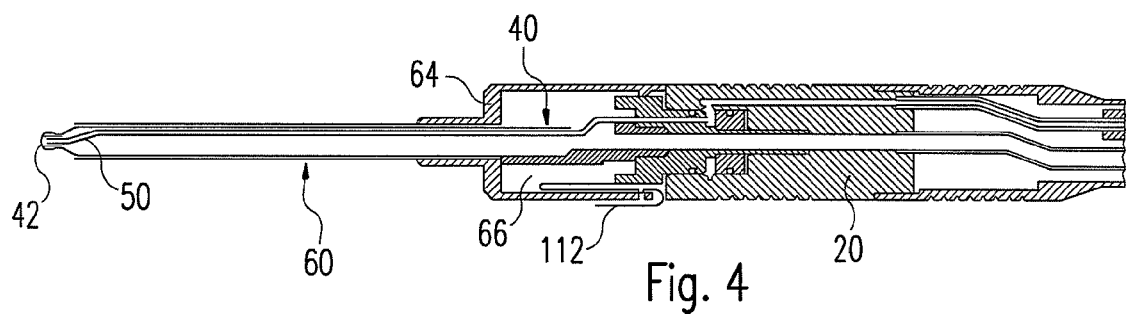
FIG. 4 is a cross sectional view of the cryosurgical instrument of FIG. 1.

FIG. 4 is a cross sectional view along the longitudinal axis of the cryosurgical instrument 10. The cavity 66, which is formed in the engaged state by the connecting piece 64 and the coupling unit 70 and extends annularly around the probe body 43, may be seen in this section. The spiral spring 114 is not shown in FIG. 4.

Figure 5:
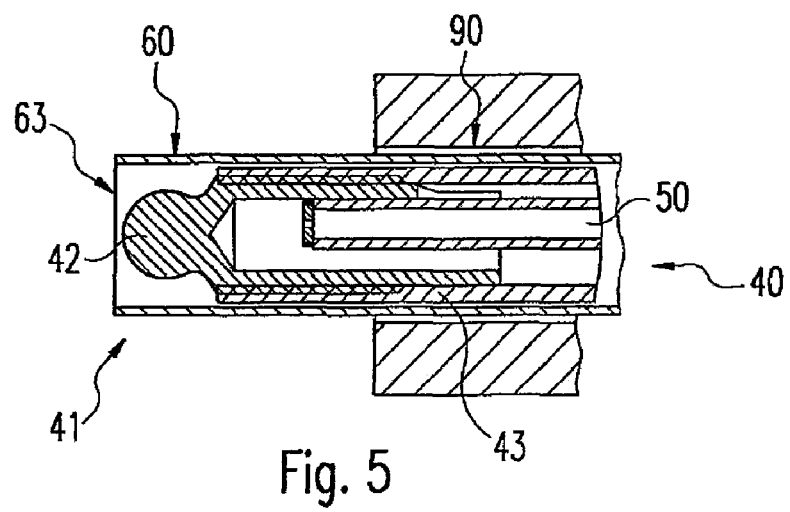
FIG. 5 is a cross sectional view of the distal end of the probe of disclosed embodiment, guided in a working channel of an endoscope and including a support tube.

The probe 40 extends along the longitudinal axis of the cryosurgical instrument through the cavity 66. For cooling the probe head 42, the probe 40 contains a gas supply line 50. The distal end 41 of the probe 40 is shown more precisely in FIG. 5, the support tube 60 being slid over the probe head 42. The probe 40 is guided in the protective tube 60, wherein at least the probe head 42 may be received in the support tube 40 and released again therefrom. FIG. 5 also shows a working channel 90 of an endoscope into which the probe 40 with the support tube 60 is introduced. The probe head 42 has a substantially spherical formation at the distal end providing an extensive region for contacting with the tissue 100. The shape of the probe head 42 assists the adhesion of tissue 100 during cooling. The distal end 62 of the support tube 60 has an attachment edge 63 which rests on the surface of the tissue for withdrawing tissue.

Figure 6:
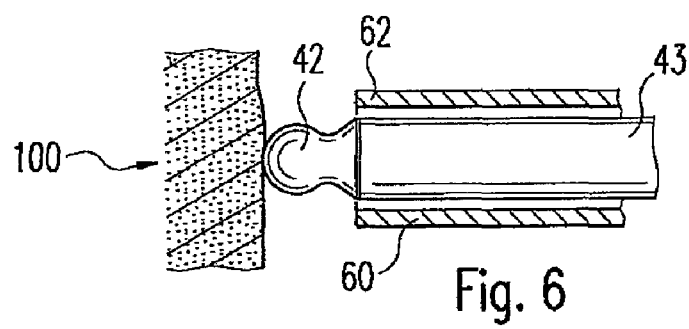
FIG. 6 illustrates a step in the process for withdrawing a tissue sample in accordance with a disclosed embodiment.
Figure 7:
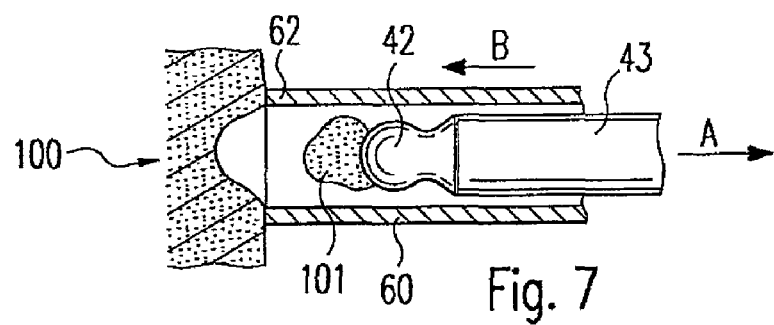
FIG. 7 illustrates a step in the process subsequent to that shown in FIG. 6, according to a disclosed embodiment.

FIGS. 6 and 7 show the withdrawal of the tissue sample 101 from the tissue 100 to be treated. In FIG. 6, the probe head 42 protrudes beyond the distal end 62 of the support tube 60 and rests on the tissue 100 to be treated. The probe head 42 is therefore in an extended position. As soon as the tissue has been frozen in certain regions onto the probe head 42, this portion, which ultimately forms the tissue sample 101, can be separated from the surrounding tissue 100 and collected in the support tube 60 by moving the probe 40 and support tube 60 counter to each other. The probe head 42 and the tissue sample 101 are then located inside the support tube 60. FIG. 7 shows this position. For the withdrawal of the tissue sample 101 according to disclosed embodiments, the support tube 60 is accelerated by the accelerating device 110 in the distal direction (cf. direction of movement B). This is a movement relative to the probe 40. As soon as the distal end 62 of the support tube 60 strikes the tissue surface of the tissue 100 to be treated, this induces a pulse on the probe 40, comprising the probe body 43 and the probe head 42. This pulse is directed counter to the direction of movement B of the support tube 60. Thus, the probe 40 is accelerated in the direction of movement A. The tissue sample 101, which is fixed to the probe head 42, is torn out of the tissue 100 to be treated.

FIGS. 8 to 12 show numerous configurations of the accelerating device 110. All of the accelerating devices 110 illustrated by way of example are integrated into a part of a gripping means 20. A probe channel 44, in which the probe 40 (not shown) is arranged, extends along the longitudinal axis of the accelerating devices 110. Preferably, the probe 40 is adhesively bonded to the gripping means 20. The connecting piece 64 is displaceable relative to the gripping means 20, and also relative to the probe 40 in the longitudinal direction (cf. direction of movement B). The support tube 60 is securely connected to the connecting piece 64. With regard to the example embodiments of FIGS. 8 to 12, it should also be noted that in this case, unlike in the exemplary embodiment from FIGS. 1 to 3, the connecting piece 64 protrudes into the gripping means.

Figure 8:
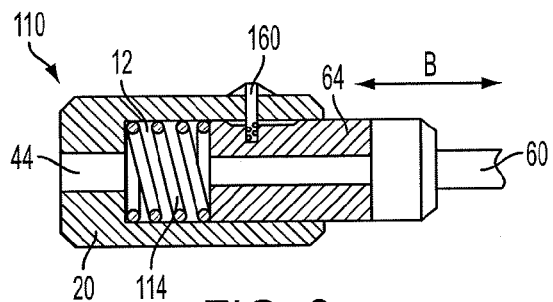
FIG. 8 illustrates a mechanical accelerating device in accordance with a disclosed embodiment.

FIG. 8 shows a first example embodiment of the accelerating device 110, the acceleration being ensured mechanically by the spiral spring 114. The spiral spring 114 is arranged in the cavity 66 which is formed by the gripping means 20 and the connecting piece 64. The spiral spring 114 is attached to both the gripping means 20 and the connecting piece 64. A triggering device 160 allows the engagement of the connecting piece 64 in a tensioned state. If required, the stored potential energy may be released by actuating the triggering device 160.

Figure 9:
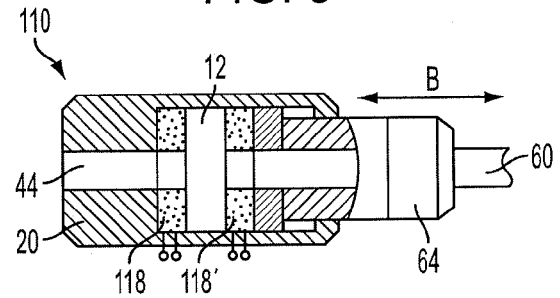
FIG. 9 illustrates an electromagnetic accelerating device in accordance with a disclosed embodiment.

FIG. 9 shows an electromagnetic accelerating device 110. Annular coils 118, 118' are arranged in the cavity 66, surrounding the probe channel 44. A first electromagnetic coil 118 is connected to the gripping means 20 and a second electromagnetic coil 118' is connected to the connecting piece 64. The electromagnetic coils 118, 118' may be activated in such a way that they either attract or repel each other. This allows the support tube 60 to be moved in the proximal or distal direction.

Figure 10:
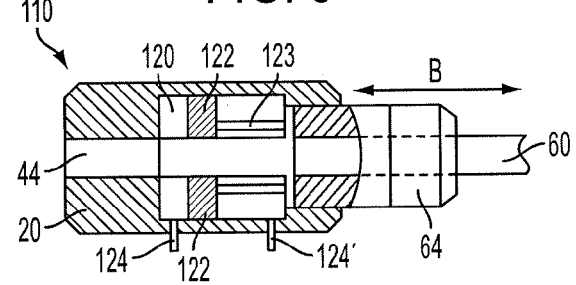
FIG. 10 illustrates a pneumatic accelerating device in accordance with a disclosed embodiment.

FIG. 10 shows a pneumatic accelerating device 110. An annular cylinder 120 is formed around the probe channel 44. A correspondingly shaped piston 122, which is connected to the connecting piece 64 via a rod linkage 123, is located in this cylinder 120. The cylinder 120, which extends substantially longitudinally in relation to the longitudinal axis of the accelerating device 110, comprises a first compressed air line 124, which opens proximally into the piston 120, and a second compressed air line 124', which opens distally into the piston 120. The piston 122 may be raised and lowered by supplying compressed air via the first compressed air line 124 or via the second compressed air line 124'. The support tube 60 is moved as a result. The acceleration of the support tube 60 may be controlled by way of corresponding metering of the compressed air.

Figure 11:
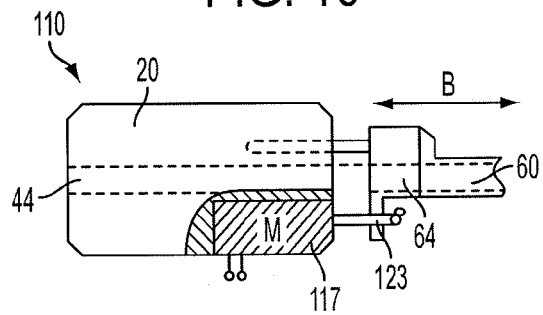
FIG. 11 illustrates an accelerating device with an electric motor in accordance with a disclosed embodiment.

FIG. 11 shows a further electromagnetic accelerating device 110. The movement of the protective tube 60 is ensured by a motor 117 which is connected to the connecting piece via a rod linkage 123.

Figure 12:
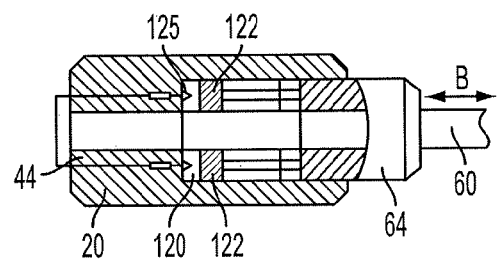
FIG. 12 illustrates a pyrotechnical accelerating device in accordance with a disclosed embodiment.

FIG. 12 shows a pyrotechnical accelerating device 110. The accelerating device 110 is constructed in a similar manner to that from FIG. 10. It comprises an annular cylinder 120 and a correspondingly annular piston 122 which is connected to the support tube 60. A pyrotechnical unit, which can be triggered by an ignition means 125, is located inside the cylinder 120. The force released by the chemical reaction is transmitted to the connecting piece 64 via the piston 122 and rod linkage 123.

It should be pointed out here that all the above described parts and in particular the details illustrated in the drawings are essential for the disclosed embodiments alone and in combination. Adaptations thereof are the common practice of persons skilled in the art.

The invention claimed is:

1. A cryosurgical instrument for obtaining a tissue sample, the instrument comprising:
    a probe with a probe head, wherein the probe head can be cooled by a cooling means, thereby fixing a portion of a tissue wall;
    a support tube, the probe being mounted in the support tube so as to be movable relative thereto; and
    an accelerating device for accelerating the support tube at a predetermined acceleration force relative to the probe, the acceleration force being directed such that the probe comes to lie inside the support tube from an extended position in which the probe head protrudes beyond a distal end of the support tube,
    wherein the distal end of the support tube is configured such that the distal end of the support tube induces, after an acceleration by the accelerating device and when coming in contact with the tissue wall, a tear-off force such that the probe head tears out the portion of the tissue wall.

2. The cryosurgical instrument according to claim 1, wherein the probe head comprises a substantially planar portion for contacting with the portion of the tissue wall.

3. The cryosurgical instrument according to claim 1, wherein the accelerating device comprises a pneumatic accelerating device.

4. The cryosurgical instrument according to claim 1, wherein the accelerating device comprises a spring for storing a predetermined amount of potential energy.

5. The cryosurgical instrument according to claim 1, wherein the accelerating device comprises a connecting piece which is operatively connected to the support tube and is coupled indirectly or directly to the probe, the connecting piece comprising a tensioning element which stores a predetermined amount of potential energy.

6. The cryosurgical instrument according to claim 5, wherein the accelerating device comprises a triggering device which releases the potential energy.

7. The cryosurgical instrument according to claim 1, further comprising a gripping piece, wherein the probe is detachably coupled to the gripping piece.

8. The cryosurgical instrument according to claim 1, wherein dimensions of the support tube and the probe are such that an overhang of the probe head in the extended position is at least 5 millimeters.

9. The cryosurgical instrument according to claim 1, wherein the support tube is made of plastics material.

10. The cryosurgical instrument according to claim 1, wherein the probe head is made of a metallic material.

11. The cryosurgical instrument according to claim 1, wherein dimensions of the support tube and the probe are such that an overhang of the probe head in the extended position is at least 15 millimeters.

12. The cryosurgical instrument according to claim 1, wherein the accelerating device comprises an electromagnetic accelerating device.

13. The cryosurgical instrument according to claim 1, wherein the accelerating device comprises a mechanical accelerating device.

14. The cryosurgical instrument according to claim 1, wherein the accelerating device comprises a pyrotechnical accelerating device.

* * * * *